(12) United States Patent
Edson et al.

(10) Patent No.: US 6,617,101 B1
(45) Date of Patent: *Sep. 9, 2003

(54) LIPOPHILIC QUENCHING OF VIRAL INACTIVATING AGENTS

(75) Inventors: Clark M. Edson, Somerville, MA (US); Andrei A. Purmal, Waltham, MA (US); Samuel K. Ackerman, Weston, MA (US)

(73) Assignee: V. I. Technologies, Inc., Watertown, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/656,243

(22) Filed: Sep. 6, 2000

Related U.S. Application Data

(63) Continuation of application No. 09/237,136, filed on Jan. 25, 1999, now Pat. No. 6,150,109.

(51) Int. Cl.$^7$ .................................................. A01N 1/02
(52) U.S. Cl. ............................ 435/2; 435/1.1; 422/28; 422/30; 422/44
(58) Field of Search .......................... 435/6, 236, 2, 435/1.1; 514/44; 536/23.1, 24.5; 422/28, 30, 44

(56) References Cited

U.S. PATENT DOCUMENTS

| | | |
|---|---|---|
| 3,487,157 A | 12/1969 | Pierce et al. |
| 3,501,557 A | 3/1970 | Brois |
| 3,636,196 A | 1/1972 | Bauer et al. |
| 4,371,472 A | 2/1983 | Okazaki et al. |
| 4,429,045 A | 1/1984 | Bass et al. |
| 4,515,906 A | 5/1985 | Friesen et al. |
| 4,567,042 A | 1/1986 | Acree et al. |
| 5,547,576 A | 8/1996 | Onishi et al. |
| 5,652,359 A | 7/1997 | Meyer et al. |
| 5,691,132 A | 11/1997 | Wollowitz et al. |
| 5,891,705 A | 4/1999 | Budowsky et al. |
| 5,919,773 A | 7/1999 | Monia et al. |
| 6,093,564 A | 7/2000 | Budowsky et al. |
| 6,093,725 A | 7/2000 | Cook et al. |
| 6,114,108 A | 9/2000 | Budowsky |
| 6,136,586 A | 10/2000 | Budowsky |
| 6,143,490 A | 11/2000 | Cook et al. |
| 6,150,109 A | 11/2000 | Edson et al. |
| 6,171,777 B1 | 1/2001 | Cook et al. |
| 6,177,441 B1 | 1/2001 | Cook et al. |
| 6,720,952 | 8/2001 | Cook et al. |
| 6,352,695 B1 | 3/2002 | Budowsky et al. |
| 6,369,048 B1 | 4/2002 | Budowsky et al. |
| 6,403,359 B1 | 6/2002 | Purmal et al. |
| 6,410,219 B1 | 6/2002 | Cook et al. |
| 2002/0034724 A1 | 3/2002 | Edson et al. |

FOREIGN PATENT DOCUMENTS

| | | |
|---|---|---|
| EP | 0 476 711 A3 | 3/1992 |
| EP | 0 476 711 A2 | 3/1992 |
| JP | 6-80520 A | 3/1994 |
| SU | 382638 | 8/1973 |
| SU | 1809836 A3 | 4/1993 |
| WO | WO 96/14737 A1 | 5/1996 |
| WO | WO 96/39818 A1 | 12/1996 |
| WO | WO 96/39820 A1 | 12/1996 |
| WO | WO 97/07674 A1 | 3/1997 |
| WO | WO 97/21346 A1 | 6/1997 |
| WO | WO 98/30327 A1 | 7/1998 |
| WO | WO 98/30545 A1 | 7/1998 |
| WO | WO 98/45415 A1 | 10/1998 |
| WO | WO 99/17802 A1 | 4/1999 |
| WO | wo 99/34791 A1 | 7/1999 |
| WO | WO 00/18412 A1 | 4/2000 |
| WO | WO 00/18969 A1 | 4/2000 |

OTHER PUBLICATIONS

US 6,331,387, 12/2001, Hei (withdrawn)

Ackerman, et al. "INACTINE™—A Potent and Selective Method for Inactivating Viruses in Contaminated Blood Products.", *25th Congress of the International Society of Blood Transfusion*, Jun. 27–Jul. 2, 1998, Oslo, Norway. Abstract No. 1305.

Amor, S,, and H.E. Webb, "Use of N–Acetylethyleneimine [AEI] for the inactivation of Semliki Forest Virus in vitro" J Medical Virology 19:367–376 (1986).

Atwell, G.J. et al., "Synthesis, DNA Interactions and Biological Activity of DNA Minor Groove Targeted Polyberizamide–linked Nitrogen Mustards," Bloorg Med. Client. Jun. 1995; 3(6):679–91.

Briel, S. et al Identification of New Aqueous Chemical Degradation Products of Isophosphoramide Mustard J Pharm Biomed Anal. Jun. 2001;25 (3–4): 669–78.

Brown, F. et al. A Universal Virus Inactivant for Decontaminating Blood and Biopharmaceutical Products Biologicals (1998) 26, 39–47.

(List continued on next page.)

Primary Examiner—John L. LeGuyader
Assistant Examiner—M Schmidt
(74) Attorney, Agent, or Firm—Wolf, Greenfield & Sacks, P.C.

(57) ABSTRACT

Methods and compositions for the inactivation and removal of contaminants of a biological composition are disclosed. The methods include the steps of: (a) contacting the biological composition with an inactivating agent including an aziridino moiety, such as ethyleneimine, an oligomer of ethyleneimine, or a haloderivative salt of either ethyleneimine or an oligomer of ethyleneimine, where a portion of the agent reacts with and inactivates the contaminant, and a portion of the agent remains unreacted; (b) contacting the product of step (a) with a lipophilic quenching agent including at least one quenching moiety attached to a lipophilic moiety, under conditions and for a time sufficient to allow the unreacted agent to bond covalently to the quenching moiety; and (c) separating the lipophilic quenching agent and the quenched inactivating agent from the biological composition.

14 Claims, 3 Drawing Sheets

OTHER PUBLICATIONS

Budowsky, E.I., "Problems and prospects for preparation of killed antiviral vaccines" Adv. Virus Res. 39:255–90 (1991).

Budowsky, et al. Inactivation of the phage MS2 Infectivity by the Action of Ethyleneimines Biorg. Khim. 11:989–991 (1985) (In Russian, English abstract).

Burrage, et al. "Inactivation of viruses by Aziridines", Advances in Transfusion Safety. Dev. Biol. Basel, Karger, 1999. vol. 102, pp. 131–139.

Charache, S. et al.. "Evaluation of Extracorporeal Alkylation of Red Cells as a Potential Treatment for Sickle Cell Anemia," Blood 1976; 47(3):481–88.

Danao, T. et al., "Nitrogen Mustard as Induction Therapy for Rheurnatoid Arthritis: Clinical and Immunologic Effects." J. Rheum. 1992 19:1683–86.

Drake, M.E. et al., "Effect of Nitrogen Mustard on Virus of Serum Hepatitis in Whole Blood." Proc. of Soc. Exp. Rio. Med. 1952(80)310–13.

Edson, et al. Abstract S277, INACTINE™—A Viral Inactivation Technology for Reducing the Infectivity of Plasma–Derived Proteins Transfusion, 1998, vol. 38, Supplement, pp. 75S.

Edson, et al. IBC 2nd International Symposium on Viral Clearance, Jun. 25–26, 1998., INACTINE™—An Inactivation Technology for Reducing the Viral Infectivity of Plasma–Derived Proteins and Red Blood Cells.

Ferguson, L.R. et al., "DNA–directed Aniline Mustards with High Selectivity for Adenine or Guanine Bases: Mutagenesis in a variety of Salmonella Typhimurium Strains Differing in DNA–Repair Capability," Mutat Res. Apr. 1994; 321(1–2):27–34.

Ferguson, L.R. et cal.. "Bacterial Mutagenicity Studies of DNA–Intercalating Aniline Mustards: an Insight Into the Mode of Action of a Novel Class of Anti–Tumor Drugs," Anticancer Drug Des. Oct. 1989; 4(3):209–19.

Fries, K.M. et al 31P NMR and Chloride Ion Kinetics of Alkylating Monoester Phosphoramidates J. Med. Chem Feb. 1991:34(2): 565–9.

Gao. Yi–Gui; Sriram, M. et cal.. "Minor Groove Binding of SN6999 to an Alkylated DNA: Molecular Structure of d(CGC[e6G]AATTCGCG)–SN6999 Complex," Biochemistry 1993, Sep. 21: 32(37):9639–48.

Gourdie T.A. et al.. "DNA–directed Alkylating Agents. 1. Structure–activity Relationships for Acridine–linked Aniline Mustards: Consequences of Varying the Reactivity of the Mustard," J. Med. Chem. Apr. 1990: 33(4):1177–86.

Gourdie T.A. et al.. "Synthesis and Evaluation of DNA–targeted Spatially Separated Bis(Aniline Mustards) as Potential Alkylating Agents with Enhances DNA Cross–linking Capability," J. Med. Chem. Jan. 1991; 34(1):240–8.

Gravatt, G.L. et al., "DNA–directed Alkylating Agents. 6. Synthesis and Antitumor Activity of DNA Tumor Groove–targeted Aniline Mustard Analogues of Pibenzimol," J. Med. Chem.. Dec. 9, 1994:37(25): 4338–45.

Gravatt, G.L. et al.. "DNA–Directed Alkylating Agents 4. 4–Anilinoduinoline–Based Minor Groove Directed Aniline Mustards," J. Med Chem 1991, 34(5):1552–60.

Griffin M.T. et al Kinetics of Activation and in Vivo Muscarinic Receptor Binding of N–(2–bromoethyl)–4–Piperidinyl Diphenylacetate: an Analog of 4–DAMP Mustard J. Pharmacol Exp Ther Jul. 1993; 266(1) 301–5.

Hamza, A. Quantum Molecular Modeling of the Interaction Between Guanine and Alkylating Agents–2–Nitrogen Mustard J. Biomol Struct Dyn Jun. 1996; 13(6):915–24.

Hartman, F.W. et al., "Preparation and Sterilization of Blood Plasma." Ant. J. Clin. Path, 1954(24); 339–48.

Hartman, F.W. et al., "On the Chemical Sterilization of Blood and Blood Plasma." Proc. of Soc.. Exp. Bio. Med. 1949;70:248–54.

Hartman, F.W., et al.. "Four–Year Study Concerning the Inactivation of Viruses in Blood and Plasma," Presented at the 55th Annual Meeting of the American Gastroenterological Association, San Francisco, California, Jun. 1954.

Hassanain, M.M., "Preliminary findings for an inactivated African horsesickness vaccine using binary ethyleneimine" Revue Elev. Med. Vet. Pays Trop. 45: 231–234 (1992).

Hemminki, K. "DNA Adducts of Nitrogen Mustards and Ethyleneimines" DNA Adducts: Identification and Biological Significance, IARC Scientific Publications No. 125, Editors: Hemminki, et al., 1994, pp. 313–321.

Hemminki, K. Reactions of Nitrogen Mustards with DNA IARC Sci. Publ 1986; (78):55–70.

Knorre, D.G. et al.. "Reactive Derivatives Of Oligonucleotides As Potential Antiviral Drugs," Problems of Virology, 1985, No. 5, pp. 524.

Kohn, K. W. et al Mechanisms of DNA Sequence Selective Alkylation of Guanine–N7 Positions by Nitrogen Mustards Biochem Pharmacol May 1, 1988; 37(9): 1799–800.

Lee, M et al., "In Vitro Cytotoxicity of GC Sequence Directed Alkylating Agents Related to Distamycin," J. Med. Cheer. 1993, Apr. 2;36(7)863–70.

Lobastov, A.E., "Use of ethylenimine dimmer for the inactivation of infectious rhinotracheitis virus of cattle" Probl. Virusol., Mol. Biol. Gistol. S–kh. Zhivotn., pp. 4–6 (1983).

LoGrippo, G.A et al.. Chemical and Combined Methods for Plasma Sterilization. , 6th Congress of the Int'l Soc. of'Blood Trans., 1958, pp. 225–230.

Mattes, W.B. et al., "GC–rich Regions in Genomes as Targets for DNA Alkylation," Carcinogenesis 1988; 9(11):2065–72.

Prakash, A.S. et al., "Differences in Sequence Selectivity of DNA Alkylation by Isomeric Intercalating Aniline Mustards," Chem. Biol. Interact. 1990; 76(23):241–8.

Price, C.C. et al Relative Reactivities for Monofunctional Nitrogen Mustard Alkylation of Nulceic Acid Components Biochim Biophys Acta Sep. 24, 1968: 166(2):327–59.

Roth, E.F. Jr. et al., "Metabolic Effects of Antisickling Amounts of Nitrogen and Nor–N itrogen Mustard on Rabbit and Human Erythrocytes." Blood 1975;45(6):779–88.

Springer, J.B. et al Isophosphoramide Mustard and Its Mechanism of Bisalkylation J. Org. Chem Oct. 16, 1998; 63(21):7218–7222.

Valu, K.K. et al., "DNA–directed Alkylating Agents. 3. Structure–activity relationships for Acridine–linked Aniline Mustards: Consequences of Varying the Length of the Linker Chain." J. Med. Chem Nov. 1990: 33(11):3014–9.

Verschaeve, L. et a. "Mutagenicity of Ethyleneimine" Mutation Res. 238:39–55 (1990).

Vlasov, V.V. et al., –The Feasibility, Of Blocking Influenza Infections By Means Of Alkylating Derivatives Of Oligonucleotides, Molecular Genetics, Microbiology, And Virology, 1984, No. 11.

Wagner, S.J. et al.. Approaches to the Reduction of Viral Infectivity in Cellular Blood Components and Single Donor Plasma. Transfusion Medicine Reviews Jan. 1991; V(1): 18–32.

Warrington, "Derivatives of Aziridine as Inactivants for Foot–and–Mouth Disease Virus Vaccines" Am J. Vet. Res., vol. 34, No. 8. pp. 1087–1091.

Wickham, G. et al., "DNA–binding Properties and Antitumour Activity of Monofunctional Alkylating Groups Attached to the DNA–intercalating Chromophore Phenanthridine: n–Brotnoalkylplienanthridinium Brodies," Biochimica et Biophysica Acta 1991 1073:528–37.

Wilke, W.S. et cal., "Parenteral Nitrogen Mustard for Inflammatory Arthritis," C'lev. Clin. J. Med. Oct. 1990; 57(7):643–46.

Yamamoto, et al. Cancer Research 26, pt. 1, 2301–2306 (Nov. 1966).

Yang, C. et al The Preparation of an Inactivated Antigen for Bluetongue Serology Zentralbl Veterinarmed [B] May 1984; 31(4); 290–6.

Zalesskaya, M.A., "Inactivation of viral genome by beta–p-ropiolactone and ethyleneimines using the bacteriophage MS–2 as an example," Russian State Library, Moscow, Russia (1988).

Zhang, Q–X. et al., Abstract S279, INACTINE™—A Method for Viral Inactivation in Red Blood Cell Concentrate Transfusion, 1998, vol. 38, Supplement, pp. 75S.

Bahnemann, Vaccine 8:299–304 (1990).

Budowsky et al., Vaccine Res. 5:29–39 (1996).

Dermer and Ham, "Ethylenimine and Other Aziridines," Chemistry and Applications, Academic Press New York and London pp 248–285 (1969).

Earley et al., "Reactions of Ethylenimines IX. The Mechanisms of Ring Openings of Ethylenimines in Acidic Aqueous Solutions," *Metcalf Chemical Laboratories of Brown University* 80:3458–3462 (1958).

Sum of w,y and z is 10-40

LIPOPHILIC QUENCHING OF VIRAL INACTIVATING AGENTS

CROSS-REFERENCE TO RELATED APPLICATIONS

This application is a continuation of U.S. Ser. No. 09/237,136, filed on Jan. 25, 1999, now U.S. Pat. No. 6,150,109.

BACKGROUND OF THE INVENTION

The invention relates to methods for quenching electrophiles.

The transmission of viral diseases (e.g., hepatitis A, B, and C infections, acquired immunodeficiency syndrome, and cytomegalovirus infection) by blood or blood products is a significant problem in medicine. Other biological compositions, such as mammalian and hybridoma cell lines, products of cell lines, milk, colostrum, and sperm, can also contain infectious viruses. Screening donor biological compositions for viral markers can help reduce the transmission of viruses to recipients, but many screening methods are directed to only a few discrete viruses, and are therefore incomplete, and may also be less than 100% sensitive. It is therefore important to inactivate viruses contained in donor blood, blood products, or other biological compositions.

A number of agents that are capable of inactivating viruses in blood have been developed. For example, ethyleneimine monomer and ethyleneimine oligomers are very effective viral inactivating agents. Methods for producing and using ethyleneimine oligomers for inactivating viruses in biological compositions are generally described in U.S. Ser. No. 08/835,446 (filed Apr. 8, 1997), U.S. Ser. No. 08/521,245 (filed Aug. 29, 1995), U.S. Ser. No. 08/855,378 (filed May 13, 1997), U.S. Ser. No. 09/005,606 (filed Jan. 12, 1998), and U.S. Ser. No. 09/005,719 (filed Jan. 12, 1998), which are hereby incorporated by reference. Ethyleneimine oligomers are themselves chemically active, and must therefore be rendered non-reactive before a product, such as blood, is used clinically. Typically, a viral inactivating compound, such as ethyleneimine dimer, is added to a biological composition to inactivate infectious viruses that might be present in the composition. A quenching agent is then added to inactivate the ethyleneimine dimer that remains after viral inactivation has taken place. The end result is a biological composition that is relatively free of infectious viruses, but that is contaminated with quenched inactivating agent and with quenching agent.

SUMMARY OF THE INVENTION

In one aspect, the invention features a method of inactivating a contaminant, such as a virus, of a biological composition; the method includes the steps of: (a) contacting the biological composition with an inactivating agent including an aziridino moiety, such as ethyleneimine, an oligomer of ethyleneimine, or a haloderivative salt of either ethyleneimine or an oligomer of ethyleneimine, where a portion of the agent reacts with and inactivates the contaminant, and a portion of the agent remains unreacted; (b) contacting the product of step (a) with a lipophilic quenching agent including at least one quenching moiety, under conditions and for a time sufficient to allow the unreacted agent to bond covalently to the quenching moiety; and (c) separating the lipophilic quenching agent and the quenched inactivating agent from the biological composition.

A preferred quenching moiety includes a nucleophilic moiety, such as a thiosulfate or thiophosphate moiety; the thiophosphate moiety may be part of an internucleotide linkage of an oligonucleotide sequence.

The inactivating agent may be, for example, ethyleneimine, an oligomer of ethyleneimine, or a haloderivative salt of either ethyleneimine or an oligomer of ethyleneimine. The biological composition may be selected from the group consisting of whole mammalian blood, purified or partially purified blood proteins, blood cell proteins, milk, saliva, blood plasma, platelet-rich plasma, a plasma concentrate, a precipitate from any fractionation of plasma, a supernatant from any fractionation of plasma, a serum, a cryoprecipitate, a cryosupernatant, a cell lysate, a mammalian cell culture, a mammalian culture supernatant, a placental extract, a product of fermentation, a platelet concentrate, a leukocyte concentrate, semen, red blood cells, and a recombinant protein-containing composition produced in a transgenic mammal. Preferably, the biological composition is whole human blood or human blood plasma. The contaminant may be a virus.

In a second aspect, the invention features a method of quenching an electrophile; the method includes contacting the electrophile with a composition including at least one thiosulfate or thiophosphate moiety attached to a second lipophilic moiety, under conditions and for a time sufficient to allow the electrophile to bond covalently to the thiosulfate or thiophosphate moiety. In preferred methods, a plurality of the thiosulfate or thiophosphate moieties are substituted with at least one $C_{1-40}$ saturated or unsaturated hydrocarbon skeleton that is unsubstituted or has between 1 and 4, inclusive, substituents, independently selected from the group consisting of hydroxyl, amino, cyano, and azido.

Preferably, the electrophile includes an aziridino moiety or a haloderivative salt. For example, the electrophile may be ethyleneimine or an oligomer of ethyleneimine.

In a third aspect, the invention features a method of removing a viral inactivating agent from a biological composition; the method includes the steps of: (a) contacting the inactivating agent with a quenching agent that is coupled to a lipophilic moiety selected from the list consisting of linear, branched, or cyclic saturated or unsaturated hydrocarbons or esters with one to forty carbons, benzyl groups, or polycyclic aromatic groups, all of which may contain hydroxyl, amino, cyano, or azido substituents; and (b) removing the inactivating agent, the quenching agent, and the lipophilic moiety from the biological composition. Preferably, step (a) includes contacting the inactivating agent with the quenching agent under conditions and for a time sufficient to allow covalent bonds to form between the inactivating agent and the quenching agent. A preferred quenching agent includes a nucleophilic moiety, such as a thiosulfate or thiophosphate moiety.

In a fourth aspect, the invention features a compound comprising (a) a lipophilic moiety; and (b) a thiosulfate or thiophosphate moiety. Preferably, the lipophilic moiety is selected from the list consisting of linear, branched, or cyclic saturated or unsaturated hydrocarbons or esters with one to forty carbons, benzyl groups, or polycyclic aromatic groups, all of which may contain hydroxyl, amino, cyano, or azido substituents. The compound may further include a reporter moiety, such as UV adsorbing or fluorescent groups. The thiophosphate moiety may be part of an internucleotide linkage of an oligonucleotide sequence.

By "quenching moiety" or "quenching agent" is meant a thiophosphate or a thiosulfate, or a compound containing a thiophosphate or a thiosulfate moiety that, when contacted with an electrophile, such as an ethyleneimine oligomer, is capable of rendering the contacted electrophile non-reactive.

By "biological composition" is meant a composition containing cells or a composition containing one or more biological molecules, or a composition containing both cells and one or more biological molecules. Cell-containing compositions include, for example, mammalian blood, red cell concentrates, platelet concentrates, leukocyte concentrates, blood plasma, platelet-rich plasma, semen, placental extracts, mammalian cell culture or culture medium, products of fermentation, and ascites fluid. Biological compositions may also be cell-free, and contain at least one biological molecule. By "biological molecule" is meant any class of organic molecule normally found in living organisms including, for example, nucleic acids, polypeptides, post-translationally modified proteins (e.g., glycoproteins), polysaccharides, and lipids. Biological molecule-containing biological compositions include, for example, serum, blood cell proteins, blood plasma concentrate, blood plasma protein fractions, purified or partially purified blood proteins or other components, a supernatant or a precipitate from any fractionation of the plasma, purified or partially purified blood components (e.g., proteins or lipids), mammalian colostrum, milk, urine, saliva, a cell lysate, cryoprecipitate, cryosupernatant, or portion or derivative thereof, compositions containing proteins induced in blood cells, and compositions containing products produced in cell culture by normal or transformed cells (e.g., via recombinant DNA or monoclonal antibody technology).

By "lipophilic moiety" is meant a moiety selected from the list consisting of linear, branched, or cyclic saturated or unsaturated hydrocarbons with one to forty carbons, benzyl groups, or polycyclic aromatic groups.

By "reporter moiety" is meant a UV adsorbing or fluorescent group which is added to the lipophilic quenching agent for the monitoring of removal of the lipophilic quenching agent and the quenched inactivating agent.

By "viral inactivating conditions" is meant the conditions under which the viral particles are incubated with the selective ethyleneimine oligomer inactivating agents of this invention, including, for example, time of treatment, pH, temperature, salt composition and concentration of selective inactivating agent so as to inactivate the viral genome to the desired extent. Viral inactivating conditions are selected from the conditions for selective modification of nucleic acids described in U.S. patent application Ser. No. 08/855,378, hereby incorporated by reference.

The invention provides new methods for the quenching of viral inactivating agents and the subsequent removal of the quenching and inactivating agents from a biological composition. This method results in a biological composition that is relatively free not only of contaminating viruses, but also relatively free of quenched (i.e., non-reactive) inactivating agent and unreacted quenching agent. The invention provides methods which are compatible with methods of removing solvent and detergent from protein-containing preparations which are virally-inactivated by a solvent/detergent method.

Other features and advantages of the invention will be apparent from the following description and from the claims.

DETAILED DESCRIPTION

Figure 1:
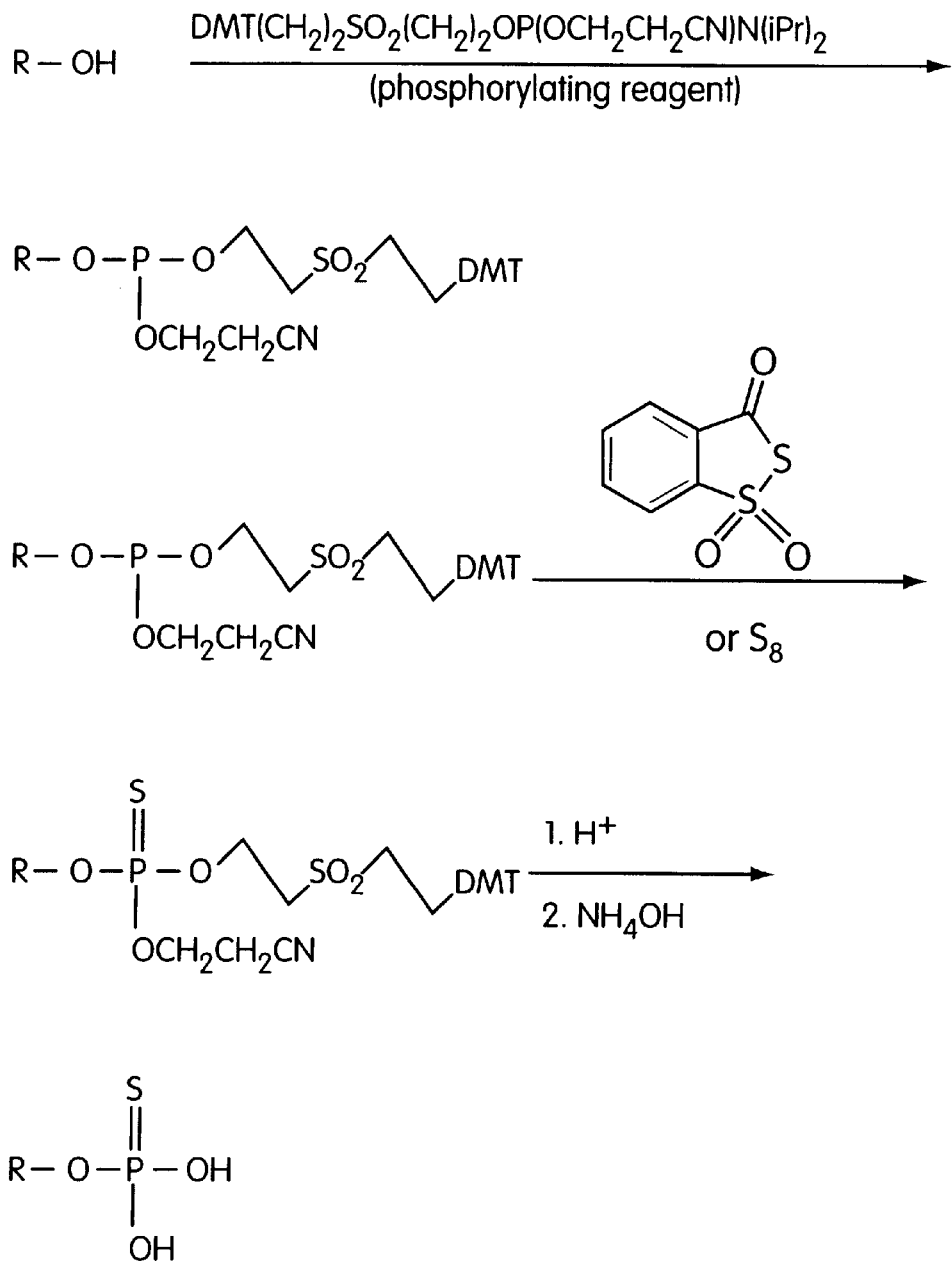
FIG. 1 is a schematic illustration showing the preparation of a lipophilic quenching agent that contains a thiophosphate group.

The invention provides general methods for quenching electrophiles with nucleophilic quenching agents, such as thiosulfate or thiophosphate moieties, that are modified so as to allow for the removal of the electrophile and the quenching agent from a biological composition.

A method of removal of quenching agent and quenched virus inactivating agent is through the use of nucleophiles, such as the thiosulfate or thiophosphate groups described above, which have attached to them lipophilic moieties. These lipophilic compounds can react with and quench electrophiles such as an ethyleneimine oligomer. This method has the added advantage that it is compatible with methods to remove solvent and detergent from protein-containing preparations which are virally-inactivated by the Solvent/Detergent procedure described by Budowsky et al., U.S. Ser. No. 09/005,719. The Solvent/Detergent method of virus activation is compatible with the virus inactivation by compounds such as ethyleneimine monomer and ethyleneimine oligomer. Thus, one can perform two methods of viral inactivation simultaneously, followed by quenching and simultaneous removal of solvent, detergent, quenching agent, and quenched ethyleneimine oligomer. Alternatively, the inactivation of viruses through the use of ethylene oligomer, followed by quenching and removal of the quenching and inactivating agents, can be performed without the use of the Solvent/Detergent method.

The thiophosphate groups used in the invention may be substituted with one substituent (e.g., [lipophilic moiety]—OP(=S)(OH)$_2$, also referred to as a thiophosphomonoester), substituted with two substituents (e.g., [lipophilic moiety]—OP(=S)(OH)(OAlk), a thiophosphodiester), or substituted with three substituents (e.g., [lipophilic moiety]—OP(=S)(OAlk)$_2$, a phosphothiotriester). The substituent may be, for example, a linear, branched, or cyclic saturated or unsaturated hydrocarbon with one to forty carbons, a benzyl group, a polycyclic aromatic group, an unsubstituted alkyl group, or an alkyl group substituted with hydroxyl, amino, azido, or cyano groups.

Polythiophosphate moieties (i.e., moieties having two or more adjacent phosphate groups) can also be used in the invention. For example, guanosine diphosphate (GDP) or guanosine triphosphate (GTP), in which one or more of the phosphate groups is a thiophosphate group, may be used in the invention. In the case of guanosine diphosphate, one or both phosphate groups may be thiophosphate groups. In the case of guanosine triphosphate, one, two, or all three of the phosphate groups may be thiophosphate groups. GDP or GTP may be attached to the lipophilic moiety, for example, at the 2' or the 3' hydroxyl group or to the heterocyclic base.

The compositions of the invention can be prepared as described below in the Examples. They can also be prepared using other standard synthetic techniques of oligonucleotide synthesis, such as those described in *Oligonucleotides and Analogs: A Practical Approach* (Eckstein ed., IRL Press 1991).

As an example, the quenching systems of the invention can be used as follows. A viral inactivating agent, such as an ethyleneimine oligomer, is added to a biological composition, as described in Budowsky, U.S. Ser. No. 08/855,378 and Budowsky et al., U.S. Ser. No. 90/005,606. At the end of the time necessary for viral inactivation, the biological composition is contacted with quenching agent, lipophilic compounds containing thiosulfate or thiophosphate groups. The biological composition and the quenching agent are allowed to remain in contact for at least one hour, at room temperature and a pH of 7.0. A 10-fold excess of thiosulfate or thiophosphate groups per equivalent of ethyleneimine oligomer is used.

The thiosulfate or thiophosphate groups react with the highly reactive moieties of the ethyleneimine compounds and become covalently linked to the ethyleneimine compounds or their haloderivative salts. When the coupled thiosulfate or thiophosphate groups are removed from the biological composition, therefore, the quenched ethyleneimine compounds are removed as well. The end result is a biological composition that is substantially free of infectious viruses, quenched ethyleneimine compounds, and quenching agent.

For example, a biological composition containing the inactivating agent ethyleneimine dimer can be quenched with sodium thiosulfate. Methods for inactivating viruses in biological matrices and quenching with thiosulfate are well known in the art and are described, for example, in Budowsky, U.S. Ser. No. 08/835,446. The thiosulfate reacts with the aziridine ring and remains covalently bound to the quenched ethyleneimine dimer.

The biological composition may include any of a number of substances. Examples of matrices include whole mammalian blood, purified or partially purified blood proteins, blood cell- proteins, milk, saliva, blood plasma, platelet-rich plasma, a plasma concentrate, a precipitate from any fractionation of plasma, a supernatant from any fractionation of plasma, a serum, a cryoprecipitate, a cryosupernatant, a cell lysate, a mammalian cell culture, a mammalian culture supernatant, a placental extract, a product of fermentation, a platelet concentrate, a leukocyte concentrate, semen, and red blood cells. Other biological matrices include those containing recombinant proteins produced in transgenic mammals. For example, the biological composition may include a protein that has been expressed in the milk of a transgenic mammal. Methods for producing such proteins are described, for example, in Wright et al., *BioTechnology* 9:830–834 (1991) and the references cited therein.

There now follow particular examples that describe the preparation of quenching systems of the invention and the use of these systems to quench viral inactivating agents. These examples are provided for the purpose of illustrating the invention, and should not be construed as limiting.

EXAMPLE 1

Preparation of a Lipophilic Quencher That Contains a Thiosulfate or Thiophosphate Group The preparation of a lipophilic quenching agent of the invention is described in FIG. 1. As shown, a lipophilic molecule (indicated as R) containing a hydroxyl group is derivatized with a phosphorylating agent. The phosphite group of the phosphorylated lipophilic molecule is oxidized to form a thiophosphate ester, which is cleaved with acid to provide a thiophosphate moiety. The product is a thiophosphate moiety that is attached to a lipophilic moiety.

Figure 2:
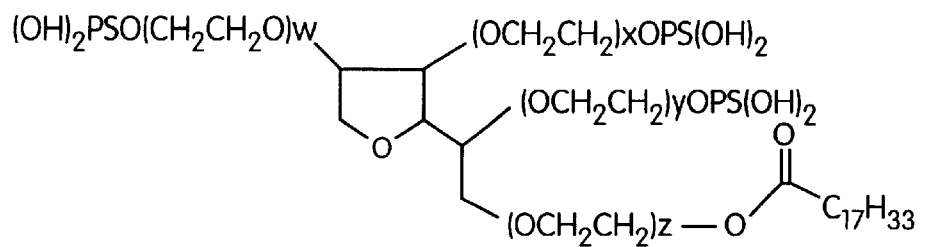
FIG. 2 is a schematic illustration showing several possible structures of lipophilic quenching agents. The T represents thymidine, which serves as an optional reporter moiety to allow for monitoring removal of quenching agent from biological compositions.
Figure 2:
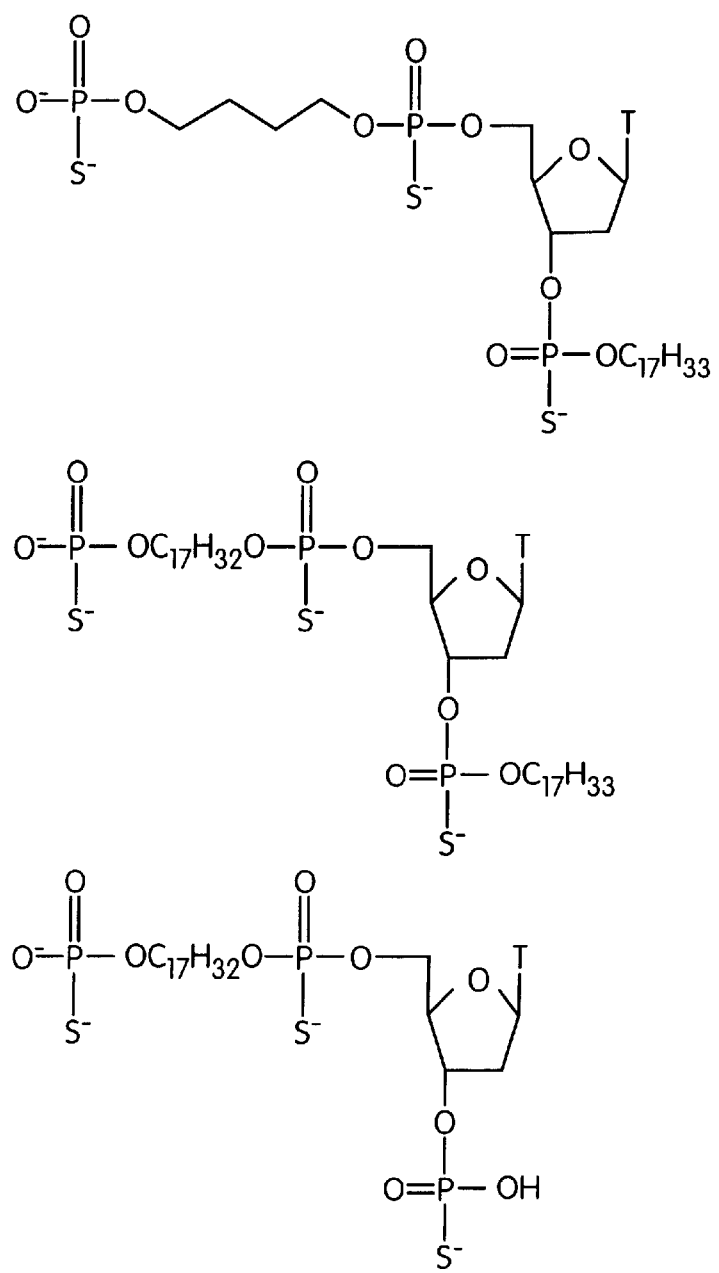
Figure 3:
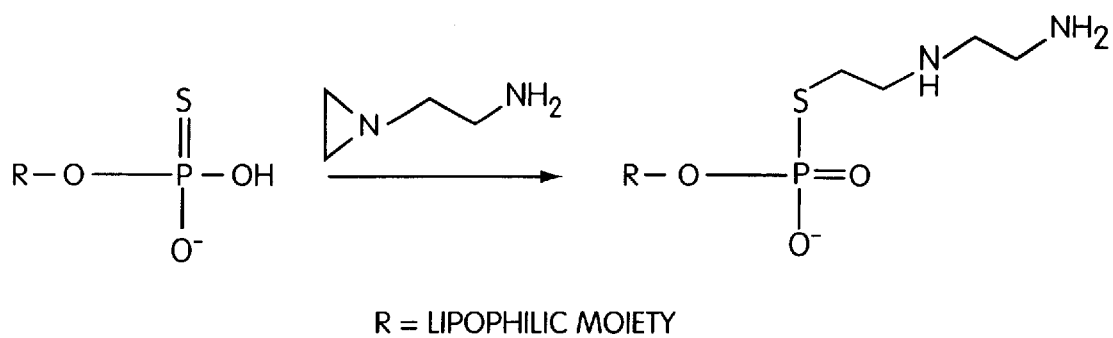
FIG. 3 is a schematic illustration of quenching of an aziridino compound, PEN102, by thiophosphate bound to a lipophilic moiety.

Many lipophilic moieties can be used for the production of the compositions of the invention. Example moieties are shown in FIG. 2. A common procedure to remove the solvent and detergent is a combination of an extraction step, such as with soybean oil, and a hydrophobic column chromatography step. Thus, it is preferred that the quenching agent and the quenched inactivating agent are readily extracted into soybean oil and able to bind to a hydrophobic column. The following properties identify a lipophilic moiety as being appropriate. One preferred property is extractability from aqueous solutions through the use of an oil, such as, for example, soybean oil. Another preferred property is affinity to a hydrophobic column, such as, for example, a C1–C18 column. These two properties allow for compatibility with the solvent/detergent method of virus inactivation. Furthermore, it is advantageous that the quenching agent be easily detectable in order to monitor its removal. In the examples provided in FIG. 2, this is fulfilled with the addition of thymidine, which is readily detected by its adsorbence of 260 nm light.

EXAMPLE 2

Quenching of an Aziridino Compound With a Thiosulfate or Thiophosphate Group That is Bound to a Lipophilic Moiety A nucleophilic thiophosphate group, which is bound to a lipophilic moiety, attacks and quenches the aziridino compound; the aziridino compound is not only rendered inactive, it also remains bonded to the quenching agent through covalent bonds.

All publications, patents, and patent applications mentioned in this specification are herein incorporated by reference to the same extent as if each individual publication or patent was specifically and individually indicated to be incorporated by reference.

Other Embodiments

From the foregoing description, it will be apparent that variations and modifications may be made to the invention described herein to adopt it to various usages and conditions. Such embodiments are also within the scope of the following claims.

What is claimed is:

1. A method of inactivating a nucleic acid-containing contaminant of an isolated biological composition, said method comprising the steps of:

(a) contacting said isolated biological composition with an inactivating agent comprising an aziridino moiety or a haloderivative thereof, wherein a portion of said agent reacts with and inactivates said contaminant, and a portion of said agent remains unreacted;

(b) contacting the product of step (a) with a lipophilic quenching agent comprising at least one nucleophilic quenching moiety attached to a lipophilic moiety, under conditions and for a time sufficient to allow the unreacted agent to bond covalently to said quenching moiety; and (c) separating said lipophilic quenching agent and said quenched inactivating agent from said isolated biological composition.

2. The method of claim 1, wherein said quenching moiety comprises a nucleophilic moiety.

3. The method of claim 2, wherein said quenching moiety comprises a thiosulfate or thiophosphate moiety.

4. The method of claim 1, wherein said quenching moiety comprises an oligonucleotide.

5. The method of claim 1, wherein said inactivating agent is ethyleneimine.

6. The method of claim 1, wherein said inactivating agent is an oligomer of ethyleneimine.

7. The method of claim 1, wherein said inactivating agent is a haloderivative salt of ethyleneimine.

8. The method of claim 1, wherein said contaminant is a virus.

9. The method of claim 1, wherein said isolated biological composition is selected from the group consisting of whole mammalian blood, purified or partially purified blood proteins, blood cell proteins, milk, saliva, blood plasma, platelet-rich plasma, a plasma concentrate, a precipitate from any fractionation of plasma, a supernatant from any fractionation of plasma, a serum, a cryoprecipitate, a cryosupernatant, a cell lysate, a mammalian cell culture, a mammalian culture supernatant, a placental extract, a product of fermentation, a platelet concentrate, a leukocyte concentrate, semen, red blood cells, and a recombinant protein-containing composition produced in a transgenic mammal.

10. The method of claim 9, wherein said isolated biological composition is whole human blood or human blood plasma.

11. A method of removing an electrophilic viral inactivating agent containing an aziridino moiety or a haloderivative thereof from an isolated biological composition, said method comprising the steps of:

(a) contacting said inactivating agent with a quenching agent comprising at least one nucleophilic quenching moiety that is coupled to at least one lipophilic moiety selected from the group consisting of linear, branched, or cyclic saturated or unsaturated hydrocarbons with one to forty carbons, benzyl groups, or polycyclic aromatic group; and (b) removing said inactivating agent, said quenching agent, and said lipophilic moiety from said isolated biological composition.

12. The method of claim 11, wherein step (a) comprises contacting said inactivating agent with said quenching agent under conditions and for a time sufficient to allow covalent bonds to form between said inactivating agent and said quenching agent.

13. The method of claim 11, wherein said quenching agent comprises a nucleophilic moiety.

14. The method of claim 11, wherein said quenching agent comprises a thiosulfate or thiophosphate moiety.

* * * * *